United States Patent [19]

Hamasaki et al.

[11] Patent Number: 4,769,318
[45] Date of Patent: Sep. 6, 1988

[54] ADDITIVE SOLUTION FOR BLOOD PRESERVATION AND ACTIVATION

[75] Inventors: Naotaka Hamasaki, Fukuoka; Shigeru Sasakawa; Masayuki Shiba, both of Tokyo, all of Japan

[73] Assignees: Ube Industries, Ltd., Ube; The Japanese Red Cross Society, Tokyo, both of Japan

[21] Appl. No.: 38,736

[22] Filed: Apr. 15, 1987

[30] Foreign Application Priority Data

Jun. 3, 1986 [JP] Japan .................................. 61-127320

[51] Int. Cl.$^4$ ........................ A01N 1/02; A61K 35/18
[52] U.S. Cl. .......................................... 435/2; 424/101
[58] Field of Search ............................ 435/2; 424/101

[56] References Cited

U.S. PATENT DOCUMENTS 4,476,221 10/1984 Kane et al. .............................. 435/2

OTHER PUBLICATIONS

Sohmer et al.-Chem. Abst. vol. 98 (1983) p. 3076p.
Hamasaki et al.-Chem. Abst. vol. 98 (1983) p. 123,476r.
Hamasaki et al.-Chem. Abst. vol. 97 (1982) p. 89637m.
Hamasaki et al., Journal of Japan Society of Blood Transfusion May 1986, vol. 32 (No. 2) pp. 204–205.

Primary Examiner—Sam Rosen
Attorney, Agent, or Firm—Frishauf, Holtz, Goodman & Woodward

[57] ABSTRACT

There is disclosed an additive solution for blood preservation and activation, which comprises a phosphoenolpyruvic acid represented by the following formula (I):

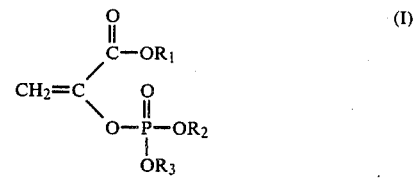

wherein $R_1$ represents a hydrogen atom or an alkyl group having 1 to 12 carbon atoms, $R_2$ and $R_3$ represent a hydrogen atom, an alkali metal or an alkyl group having 1 to 12 carbon atoms respectively, a saccharide, adenine and an organic acid and/or a pharmaceutically acceptable alkali metal salt of the organic acid.

8 Claims, No Drawings

ADDITIVE SOLUTION FOR BLOOD PRESERVATION AND ACTIVATION

BACKGROUND OF THE INVENTION

This invention relates to an additive solution for blood preservation and activation.

In our country, heretofore, a blood preservative comprising sodium citrate, citric acid and glucose (abbreviated as ACD solution) or a blood preservative comprising sodium citrate, citric acid, glucose and sodium dihydrogen phosphate dihydrate (CPD) has been used for preservation of collected blood. On the other hand, in Europe and the United States of America, a blood preservative comprising sodium citrate, citric acid, glucose, sodium dihydrogen phosphate dihydrate and adenine has been used.

However, even when blood is preserved by use of the blood preservative as described above, there ensue the following problems:

(1) the shape of erythrocyte changes during preservation;

(2) the oxygen releasing ability of hemoglobin in erythrocytes decreases during storage;

(3) hemolysis occurs excessively in erythrocytes with high hematocrit value (abbreviated as Ht value) [more specifically, Ht indicates the corporeal components in blood (erythrocyte, platelet and leukocyte) as represented by $$Ht = \frac{\text{corporeal components}}{\text{whole blood}} \times 100,$$

and most of the corporeal components are erythrocytes. And, erythrocyte concentrates under the present situation have Ht values of 70 to 80%, and the blood preservatives under the present situation have been said to be unsuitable for preservation of erythrocyte concentrates with high Ht values of over 80%. Normal human Ht values are said to be 36 to 48% for men and 34 to 42% for women].

Such problems are becoming extremely important in recent years as the demand for component therapy, that is, platelet, leukocyte and plasma-poor erythrocyte concentrate increases. In other words, while an increase in separation ratio of plasma, platelets, leukocytes, etc. from the collected blood to obtain a high Ht value may have the advantage in increasing the amount of plasma fractionation products and alleviating trouble during transfusion (for example, side effects accompanied with leukocytes such as pyrexia, antibody production, etc.), enhancement of separation of plasma, platelets, leukocytes, etc., other than erythrocytes from the collected blood will result in such problems mentioned above, that is the oxygen releasing ability of erythrocytes is further reduced, the shape of the erythrocyte changes and hemolysis occurs excessively.

SUMMARY OF THE INVENTION

Accordingly, the present invention is to provide an additive solution for blood preservation and activation which is effective for prevention of change in shape of erythrocytes, reduction of oxygen releasing ability of erythrocytes and hemolysis in a preserved blood, particularly erythrocyte concentrates.

The present inventors have studied intensively on cell membrane permeability and energy metabolism of erythrocytes and consequently found an effective additive solution which is effective for functional activation of erythrocytes and also effective for strengthening cell membrane to accomplish the present invention.

More specifically, the present invention concerns an additive solution for blood preservation and activation, comprising a phosphoenolpyruvic acid represented by the following formula (I):

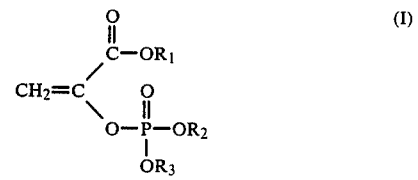

wherein $R_1$ represents a hydrogen atom or an alkyl group having 1 to 12 carbon atoms, $R_2$ and $R_3$ represent a hydrogen atom, an alkali metal or an alkyl group having 1 to 12 carbon atoms respectively, a saccharide, adenine and an organic acid and/or a pharmaceutically acceptable alkali metal salt of said organic acid.

DESCRIPTION OF THE PREFERRED EMBODIMENTS

In the phosphoenolpyruvic acid represented by the formula (I), when $R_1$, $R_2$ or $R_3$ is an alkyl group having 1 to 12 carbon atoms, it may specifically be a methyl group, an ethyl group, an n-propyl group, an isopropyl group, an n-butyl group, an isobutyl group, a sec-butyl group, a tert-butyl group, an n-amyl group, an isoamyl group, a sec-amyl group, an active amyl group, a tert-amyl group, an n-hexyl group, an n-heptyl group, an n-octyl group, an n-nonyl group, an n-decyl group, an n-undecyl group, an n-dodecyl group or the like.

When $R_2$ and $R_3$ are alkali metals, they may be specifically sodium or potassium, etc.

However, since phosphoenolpyruvic acid is usually available as sodium phosphoenolpyruvate hydrate, it is preferable to use a sodium salt hydrate.

In the present invention, specific examples of the saccharide may include sucrose, maltose, galactose, mannitol or the like.

Further, in the present invention, an organic acid and its pharmaceutically acceptable organic acid salt are used, preferably organic acids which do not exhibit strong toxicity in living bodies or which are known to exist in living bodies and salts of such organic acids. For example, there may be included citric acid—sodium citrate, acetic acid—sodium acetate, pyruvic acid—sodium pyruvate, lactic acid—sodium lactate, tartaric acid—sodium tartarate, etc. These organic acids and salts are preferred, because they function as a buffer for pH control, and also have the action of inhibiting formation of fibrin which causes blood clotting.

The additive solution for blood preservation and activation of the present invention should preferably be used in the form of a solution. For example, in an additive solution containing monosodium phosphoenolpyruvate; sucrose, maltose or mannitol; adenine; and citric acid and/or trisodium citrate, it is preferred that 10 to 100 mmole/liter of monosodium phosphoenolpyruvate, 100 to 300 mmole/liter of sucrose, maltose or mannitol, 0.2 to 2 mmole/liter of adenine and 3 to 50 mmole/liter of citric acid and/or trisodium citrate should be contained and the osmolarity should be adjusted with sodium chloride (280–350 mOsm/kg). More preferably, monosodium phosphoenolpyruvate is added in an amount of 50 to 100 mmole/liter to the additive solution. Otherwise, if necessary, phosphoric acid or an alkali metal salt thereof such as sodium phosphate may be also added.

When using the above prepared solution, it should preferably be added in an amount of 30 to 150 ml per 100 ml of collected blood.

In the present invention, the mixture of the additive solution of the present invention and blood such as an erythrocyte concentrate may preferably be incubated immediately before transfusion, whereby improvements in both 2,3-DPG and ATP values can be seen.

In the additive solution for blood preservation and activation of the present invention, the phosphoenolpyruvic acid represented by the above formula (I) permeates through the cell membranes of erythrocytes and produces 2,3-diphosphoglycerate (abbreviated as 2,3-DPG) and adenosine triphosphate (abbreviated as ATP) through the glycolytic metabolism in erythrocytes. The 2,3-DPG plays a role in controlling oxygen affinity of erythrocytes, and prevents reduction of oxygen releasing ability of erythrocytes during blood preservation. Adenine also permeates through the cell membrane of erythrocytes and produces ATP in erythrocytes. The ATP thus formed within cells contributes to phosphorylation of cell membrane, maintenance of erythrocyte shape and survival of erythrocytes in vivo and/or in vitro. On the other hand, the saccharide contributes to strengthen cell membrane of erythrocytes and maintains the structure of erythrocytes to prevent hemolysis. Further, the organic acid and pharmaceutically acceptable alkali metal salt of organic acid plays a role in discharging carbon dioxide in erythrocytes and maintaining acid-base equilibrium associated therewith during preservation of blood. Particularly, when containing citric acid and/or sodium citrate, they will not permeate through the cell membranes of erythrocytes, but have buffering action to be effective for maintaining pH and also effective in inhibiting fibrin formation which causes aggregation of erythrocytes to occur.

EXAMPLES

The present invention is described in more detail below by referring to Examples and Test examples.

EXAMPLE 1

Composition of an additive solution for blood preservation and activation

One liter of an aqueous solution was made up by dissolving 61.56 g (180 mmole) of sucrose, 2.58 g (10 mmole) of trisodium citrate, 0.94 g (6 mmole) of sodium dihydrogen phosphate dihydrate, 0.068 g (0.5 mmole) of adenine and 6.24 g (30 mmole) of monosodium phosphoenolpyruvate monohydrate in water.

EXAMPLE 2

Composition of an additive solution for blood preservation and activation

One liter of an aqueous solution was made up by dissolving 61.56 g (180 mmole) of sucrose, 5.16 g (20 mmole) of trisodium citrate, 0.96 g (6 mmole) of sodium dihydrogen phosphate dihydrate, 0.068 g (0.5 mmole) of adenine and 10.40 g (50 mmole) of monosodium phosphoenolpyruvate monohydrate in water.

EXAMPLE 3

Composition of an additive solution for blood preservation and activation

One liter of an aqueous solution was made up by dissolving 23.66 g (130 mmole) of mannitol, 2.58 g (10 mmole) of trisodium citrate, 0.94 g (6 mmole) of sodium dihydrogen phosphate dihydrate, 0.068 g (0.5 mmole) of adenine and 10.40 g (50 mmole) of monosodium phosphoenolpyruvate monohydrate in water.

EXAMPLE 4

Composition of an additive solution for blood preservation and activation

One liter of an aqueous solution was made up by dissolving 44.46 g (130 mmole) of maltose, 2.58 g (10 mmole) of trisodium citrate, 0.94 g (6 mmole) of sodium dihydrogen phosphate dihydrate, 0.068 g (0.5 mmole) of adenine and 10.4 g (50 mmole) of monosodium phosphoenolpyruvate monohydrate in water.

TEST EXAMPLE (1) Preparation of erythrocyte concentrate

Human peripheral blood was collected in a blood bag and centrifuged to separate leukocytes, platelets and plasma, etc., thus obtaining an erythrocyte concentrate with a hematocrit value of 90 to 95%.

(2) Changes with lapse of time when stored at 4°–6° C.

To 150 ml of the erythrocyte concentrate obtained in (1) was added 150 ml of the additive solution prepared in Example 1. The mixture was stored at 4°–6° C., and sampling was practised every one week, and 2,3-DPG and ATP amounts in erythrocytes and hemoglobin amounts in suspension solution were measured. The results are shown in Table 1.

TABLE 1

| Storage period (week) | Changes with storage period in erythrocyte or suspension solution when stored at 4−6° C. | | |
|---|---|---|---|
| | Component of erythrocyte | | Hb in suspension solution[a] (mg/100 ml) |
| | 2,3-DPG (μmole/gHb) | ATP (μmole/gHb) | |
| 0 | 14 | 5.6 | 4.3 |
| 1 | 6.9 | 6.7 | 11 |
| 2 | 3.8 | 6.5 | 19 |
| 3 | 0.3 | 3.4 | 15 |
| 4 | 0.1 | 1.9 | 30 |
| 5 | 0.2 | 0.9 | 69 |
| 6 | 0.1 | 0.6 | 132 |

[a]Indicating the extent of hemolysis, and hemolysis is more severe as the value is greater.

Thus, by addition of the additive solution prepared in Example 1 to the erythrocyte concentrate, 2,3-DPG and ATP in the stored blood can be maintained over a long term to make it clear that no remarkable hemolysis of blood cells has occurred during this period. Particularly, although 2,3-DPG is abruptly lowered, the value at 2 weeks is slightly improved as compared with the case when no monosodium phosphoenolpyruvate is added.

(3) Changes with storage period when stored at 4° C. and incubated at 37° C. for 60 minutes before measurement The same experiment as (2) was introduced except that the mixture of the erythrocyte concentrate obtained in (1) and the additive solution prepared in Example 1 was incubated before measurement at 37° C. for 60 minutes. The results are shown in Table 2.

TABLE 2

Changes with storage period in the erythrocyte or suspension solution when incubated at 37° C. for 60 minutes

| Storage period (week) | Component of erythrocyte | | Hb in suspension solution[a] (mg/100 ml) |
|---|---|---|---|
| | 2,3-DPG (μmole/gHb) | ATP (μmole/gHb) | |
| 0 | 23 | 7.4 | 16 |
| 1 | 11 | 7.2 | 12 |
| 2 | 7.3 | 7.0 | 17 |
| 3 | 2.4 | 6.2 | 18 |
| 4 | 1.0 | 5.3 | 33 |
| 5 | 0.5 | 3.4 | 76 |
| 6 | 0.4 | 2.9 | 134 |

[a] Indicating the extent of hemolysis, and hemolysis is more severe as the value is greater.

When incubation-treatment at 37° C. is carried out immediately before transfusion, improvements to great extent can be seen in both 2,3-DPG and ATP values, thus exhibiting clearly the effect of addition of sodium phosphoenolpyruvate.

(4) Changes with storage period when the additive solution prepared in Example 2 is used The same test as (3) was conducted except for adding 150 ml of the additive solution prepared in Example 2 to 150 ml of the erythrocyte concentrate obtained in (1). The results are shown in Table 3.

TABLE 3

Changes with storage period of the erythrocyte or suspension solution when incubated at 37° C. for 60 minutes

| Storage period (week) | Component of erythrocyte | | Hb in suspension solution[a] (mg/100 ml) |
|---|---|---|---|
| | 2,3-DPG (μmole/gHb) | ATP (μmole/gHb) | |
| 0 | 45 | 6.2 | 12 |
| 1 | 35 | 6.8 | 21 |
| 2 | 23 | 6.3 | 22 |
| 3 | 14 | 6.0 | 28 |
| 4 | 9 | 5.7 | 37 |
| 5 | 8 | 4.9 | 50 |
| 6 | 6 | 4.2 | 59 |

[a] Indicating the extent of hemolysis, and hemolysis is more severe as the value is greater.

(5) Changes with storage period when the additive solution prepared in Example 3 is used The same test as (3) was conducted except for adding 100 ml of the additive solution prepared in Example 3 to 150 ml of the erythrocyte concentrate obtained in (1). Otherwise, incubation was performed at 37° C. for 30 minutes. The results are shown in Table 4.

TABLE 4

Changes with storage period of the erythrocyte or suspension solution when incubated at 37° C. for 30 minutes

| Storage period (week) | Component of erythrocyte | | Hb in suspension solution[a] (mg/100 ml) |
|---|---|---|---|
| | 2,3-DPG (μmole/gHb) | ATP (μmole/gHb) | |
| 0 | 45 | 6.2 | 14 |
| 1 | 35 | 6.8 | 22 |
| 2 | 23 | 6.2 | 24 |
| 3 | 14 | 6.0 | 28 |

TABLE 4-continued

Changes with storage period of the erythrocyte or suspension solution when incubated at 37° C. for 30 minutes

| Storage period (week) | Component of erythrocyte | | Hb in suspension solution[a] (mg/100 ml) |
|---|---|---|---|
| | 2,3-DPG (μmole/gHb) | ATP (μmole/gHb) | |
| 4 | 9 | 5.7 | 38 |
| 5 | 8 | 5.0 | 50 |
| 6 | 6 | 4.2 | 59 |

[a] Indicating the extent of hemolysis, and hemolysis is more severe as the value is greater.

(6) Changes with storage period when the additive solution prepared in Example 4 is used The same test as (3) was conducted except for adding 100 ml of the additive solution prepared in Example 4 to 150 ml of the erythrocyte concentrate obtained in (1). Otherwise, incubation was performed at 37° C. for 30 minutes. The results are shown i Table 5.

TABLE 5

Changes with storage period in the erythrocyte or suspension solution when incubated at 37° C. for 30 minutes

| Storage period (week) | Component of erythrocyte | | Hb in suspension solution[a] (mg/100 ml) |
|---|---|---|---|
| | 2,3-DPG (μmole/gHb) | ATP (μmole/gHb) | |
| 0 | 45 | 6.1 | 14 |
| 1 | 35 | 6.8 | 20 |
| 2 | 23 | 6.3 | 22 |
| 3 | 14 | 6.0 | 25 |
| 4 | 9 | 5.6 | 35 |
| 5 | 8 | 4.9 | 50 |
| 6 | 6 | 4.2 | 57 |

[a] Indicating the extent of hemolysis, and hemolysis is more severe as the value is greater.

Even after 6 weeks, the activities of the stored erythrocyte were maintained at extremely high levels, with 2,3-DPG and ATP being comparable with those in fresh blood, thus indicating clearly efficacy of the present preservative.

Thus, in erythrocyte concentrates, the concentrations of 2,3-DPG and ATP within erythrocytes are higher at initiation of preservation than in fresh blood, and the concentrations of 2,3-DPG and ATP within erythrocytes of the stored blood are maintained at the equal level to fresh blood even after 6 weeks, and also hemolysis is extremely slight. Thus, it has been found that the activities of blood cells after preservation can be maintained at an extremely high level.

According to the additive solution for blood preservation and activation of the present invention, it is possible to preserve the blood with maintenance of activities of erythrocytes for a long period in a collected blood, particularly applied to erythrocyte concentrate having high Ht value.

What we claimed are:

1. An additive solution for blood preservation and activation, comprising 10 to 100 mmole/liter of a phosphoenolpyruvic acid represented by the following formula (I):

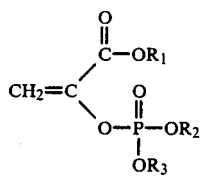 (I)

wherein $R_1$ represents a hydrogen atom or an alkyl group having 1 to 12 carbon atoms, $R_2$ and $R_3$ each independently represent a hydrogen atom, an alkali metal or an alkyl group having 1 to 12 carbon atoms; 100 to 300 mmole/liter of a saccharide, 0.2 to 2 mmole/liter of adenine; and 3 to 50 mmole/liter of an organic acid and/or a pharmaceutically acceptable alkali metal salt of said organic acid.

2. The additive solution for blood preservation and activation according to claim 1, wherein said saccharide is sucrose, maltose, galactose or mannitol.

3. The additive solution for blood preservation and activation according to claim 1, wherein said organic acid is citric acid and said pharmaceutically acceptable alkali metal salt of the organic acid is sodium citrate.

4. The additive solution for blood preservation and activation according to claim 1, comprising an aqueous solution containing 10 to 100 mmole/liter of monosodium phosphoenolpyruvate, 100 to 300 mmole/liter of sucrose, maltose or mannitol, 0.2 to 2 mmole/liter of adenine and 3 to 50 mmole/liter of citric acid and/or trisodium citrate.

5. The additive solution for blood preservation and activation according to claim 4, wherein an amount of monosodium phosphoenolpyruvate is 50 to 100 mmole/liter.

6. A method for blood preservation and activation comprising mixing an effective amount of the additive solution according to claim 1 and blood and thereafter carrying out an incubation treatment immediately before transfusion.

7. The additive solution of claim 4 further comprising sodium chloride added to adjust osmolarity of the aqueous solution.

8. The method of claim 6 wherein the incubation treatment to be carried out immediately before transfusion comprises incubating the additive solution and blood mixture at 37° C.

* * * * *